United States Patent [19]

Narayanan et al.

[11] 4,065,563
[45] Dec. 27, 1977

[54] 3-HETERO-5-ISOTHIOCYANOPHENYL OXADIAZOLES AS ANTIFUNGAL AND ANTIBACTERIAL AGENTS

[75] Inventors: Venkatachala L. Narayanan, Hightstown, N.J.; Hans H. Gadebusch, Yardley, Pa.; Rudiger D. Haugwitz, Titusville, N.J.

[73] Assignee: E. R. Squibb & Sons, Inc., Princeton, N.J.

[21] Appl. No.: 761,091

[22] Filed: Jan. 21, 1977

Related U.S. Application Data

[62] Division of Ser. No. 555,511, March 5, 1975, Pat. No. 4,022,901.

[51] Int. Cl.$^2$ .................... A61K 31/38; A61K 31/42
[52] U.S. Cl. .................................... 424/272; 424/258
[58] Field of Search ........................................ 424/272

[56] References Cited
U.S. PATENT DOCUMENTS 3,853,893   12/1974   Narayanan et al. ............ 260/294.8 E

*Primary Examiner*—Raymond V. Rush
*Attorney, Agent, or Firm*—Lawrence S. Levinson; Merle J. Smith; Burton Rodney

[57] ABSTRACT

Compounds are provided having the formula

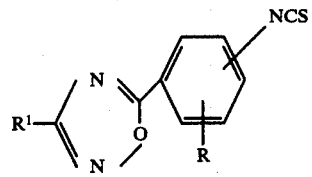

which compounds are useful as anthelmintics, and antifungal and anti-bacterial agents. In addition, methods for preparing such compounds, intermediates prepared in such methods, useful compositions containing such compounds and methods for employing such compounds and compositions containing the same are also provided.

9 Claims, No Drawings

3-HETERO-5-ISOTHIOCYANOPHENYL OXADIAZOLES AS ANTIFUNGAL AND ANTIBACTERIAL AGENTS

This is a division, of application Ser. No. 555,511, filed Mar. 5, 1975, now U.S. Pat. No. 4,022,901.

This invention relates to compounds of the formula:

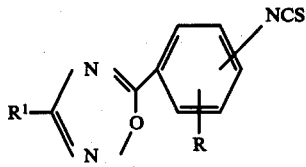

wherein R is hydrogen, lower alkyl, aryl, halogen, trifluoromethyl, lower alkoxy, aryloxy, di(lower alkyl)amino and

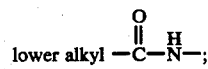

and $R^1$ is a monocyclic 5- or 6-membered heterocyclic containing a hetero atom such as sulfur, oxygen, or nitrogen, and which may optionally contain one or more other hetero atoms such as oxygen, nitrogen or sulfur, or a bicyclic 9- or 10-membered heterocyclic containing at least one hetero atom, such as nitrogen, oxygen, or sulfur, in at least one of the rings, and which may optionally contain one or more other hetero atoms such as oxygen, nitrogen or sulfur in either of said rings.

In addition, this invention encompasses the methods for preparing the above 3-hetero-(isothiocyanophenyl)oxadiazoles, compositions containing the 3-hetero-(isothiocyanophenyl)oxadiazoles and methods for using said compositions as anthelmintic agents, anti-fungal agents and anti-bacterial agents.

Lastly, this invention is intended to also include the intermediates utilized in preparing such 3-hetero(isothiocyanophenyl) oxadiazoles.

The term "aryl" is intended to include phenyl, naphthyl and substituted phenyl wherein said substitutent may be fluoro, chloro, bromo, iodo, nitro, trifluoromethyl, lower alkyl and lower alkoxy.

The term "lower alkyl" is intended to mean a straight or branched, hydrocarbon fragment of from one to ten carbon atoms, preferably one to four carbons, such as methyl, propyl, t-butyl, and the like.

The term "lower alkoxy" is intended to mean a lower alkyl group linked through a single bond to oxygen.

The term "halo or halogen" is intended to mean "chloro", "bromo", or "fluoro".

The $R^1$ heterocyclic substituents may contain 1 to 3 hetero atoms and include thienyl, furyl, thiazolyl, isothiazolyl, pyridyl, pyrryl, pyrazinyl, pyrimidinyl, quinolinyl, imadazolyl, oxazolyl, piperazinyl, thiadiazolyl and triazolyl. The heterocyclic substituent may, if desired, be substituted at a carbon atom, or at a secondary nitrogen atom (where present) with a lower alkyl group, lower alkoxy group, or a halogen. The heterocyclic ring is attached at any available carbon atom as for example 2-, 3-, or 4-pyridyl; 2- or 3-thienyl; or 2- or 3-furyl, etc.

The compounds of this invention are prepared in the following manner.

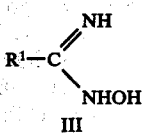

Nitriles of formula II are converted to amidoximes of the formula III by treatment with an acid salt of hydroxylamine, such as the hydrochloride, sulfate or phosphate in the presence of an acid acceptor, such as sodium or potassium carbonate. The reaction is generally conducted in an aqueous or non-aqueous alcohol solvent of up to four carbon atoms at from about room temperature to the reflux temperature of the solvent for periods of from one to 48 hours, preferably about 48 hours.

Heating compounds of formula III with a compound of formula VI gives nitrophenyloxadiazoles of formula IV. The reaction may be run in an inert organic solvent, such as benzene, toluene, tetrahydrofuran, diglyme. The temperature range generally employed is either the refluxing temperature of the solvent or about 100° which ever is the lesser, and the time ranges from about a few minutes to about eight hours. This reaction is preferably conducted in the presence of a catalytic amount of $BF_3$-etherate.

Compounds of the type IV are reduced to compounds of the formula V either catalytically using $PtO_2/H_2$ or $Pd/H_2$ preferably in the presence of about 2–5 equivalents of acid, such as HCl or $H_2SO_4$ or chemically, for example, using $Na_2S_2O_4/CH_3OH$, $N_2H_4$, Sn/HCl, or $NaBH_2S_3$.

The conversion of the amines of formula V into the 3-hetero-(isothiocyanophenyl)oxazoles (I) of this invention may be achieved by reacting the amine with:

a) ClCCl (C=S)

in a relatively non-polar solvent, such as chloroform, ether, tetrahydrofuran, etc., preferably in the presence of an acid acceptor, such as calcium carbonate, trimethylamine, etc. at temperatures from 0° to 60° C. More specific reaction procedures are disclosed in Houben-Weyl, 4th Edition, Vol. 9, pages 867 and 88 (1955) and the use of acid binding agents is disclosed in Arch. Pharm. 295, 146-151 (1962).

b. N,N-di(lower alkyl)thiocarbamoyl halide, wherein said halo atom is chlorine or bromine, in an organic solvent, such as benzene, toluene, ethylene dichloride or chlorobenzene at temperatures of from about 40° to about 200° C [J. Org. Chem. 30, 2465 (1965)].

c. a bis-thiocarbamoyl sulfide of the formula

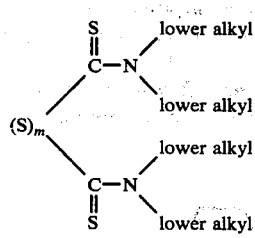

wherein m is one or two and lower alkyl (preferably ethyl) in the presence of a hydrogen halide at room temperature to the refluxing temperature of the organic solvent used, such as chlorobenzene [Helv. Chim. Acta 49, 1716 (1966)].

d. bis-trichloromethyl penta-thiodiperoxycarbamate wherein said amine is present in an excess (3:1) [Angew. Chem. 78, 985 (1966)].

e. ammonium rhodanide in the presence of gaseous hydrogen chloride in the manner shown in British Patent 1,099,768.

f. phosgene and phosphorus pentasulfide in the general manner described in Houben-Weyl, 4th Edition, Vol. 9, pages 867 and 88 (1955).

g. carbon disulfide in the presence of an inorganic or organic base, such as triethylamine, potassium carbonate, etc. followed by oxidative dehydrosulphurisation with a metal salt (British Pat. No. 793,802) such as lead, copper, zinc or iron (III) salts, iodine, alkali metal hypochlorites or chlorites, preferably the sodium or potassium salts (French Pat. No. 1,311,855), acid halides such as phosgene and phosphorus oxychloride [Chem. Ber. 98, 2425-2426 (1965)], chlorine and ammonium sulfide (DAS 1,198,189) or chloramine T (British Patent No. 1,024,913).

h. ammonium rhodanide and benzoyl chloride, followed by thermal decomposition in a refluxing solvent such as chlorobenzene [Houben-Weyl, 4th Edition, 9, 867 and 88 (1955)].

i. carbon disulfide, dicyclohexyl carbodiimide and a tertiary amine such as pyridine or triethylamine at temperatures of from about −10° to about 30° C for from about 5 to about 24 hours [Chem. Ber. 101, 1746 (1968)].

j. carbon disulfide and butyl lithium [J. Org. Chem. 39, 1970 (1974)].

The publications cited for the introduction of the isothiocyano group are incorporated by reference.

The product may be purified by recrystallization from solvents such as benzene, ethyl acetate, chloroform, acetonitrile, petroleum ether, benzene-petroleum ether or chromatographed over silica or alumina column.

The starting materials of formulae II and VI are known compounds and/or are easily prepared from known materials employing conventional procedures as will be apparent to those skilled in the art.

The preferred compounds and starting materials prepared by the above procedures are those wherein R is hydrogen, halogen, such as chlorine, lower alkyl, such as methyl, and lower alkoxy, such as ethoxy, and $R^1$ is thienyl, furyl, pyridyl, thiazolyl, isothiazolyl, quinolinyl, pyrimidinyl, pyrizinyl, and N-methyl pyrryl and especially where the -NCS group is located in the para position. Most preferred are those compounds wherein $R^1$ is thienyl, furyl, or pyridyl.

The compounds of the present invention have antifungal activity, anti-bacterial activity and anthelmintic activity.

The compounds of the invention have activity against gram-positive bacteria and fungi in that they inhibit these organisms when tested in conventional in vitro tube dilution or agar dilution assays at low levels and are useful in the treatment and/or prevention of (a) superficial dermatoses, bacterial or fungal diseases of mammalian species such as dogs, cats, rats and mice due to species of Staphylococcus, Streptococcus, Corynebacterium, Erysipelothrix, Candida, Trichophyton, Microsporum and Epidermophyton, (b) deep mycoses, fungal diseases of such mammalian species due to Candida, Cryptococcus, Blastomyces, Histoplasma and similar organisms, and (c) thrush, fungal disease in poultry due to Candida species, principally Candida albicans. In treating affected hosts, the compounds for (a) may be applied topically to the affected area or lesion as a 0.5-2% cream or ointment formulation to the affected area on the skin for 14 or more days or given orally in daily dosages of about 10-200 mg per kilogram of body weight, for (b) given parenterally in daily doses by injection of about 10-50 mg per kilogram body weight, and for (c) given orally or vaginally or in the case of poultry, may be mixed at a level of 30-100 mg per quart of water or lb. of feed. When the compounds are to be employed primarily as prophylactic agents (poultry) the daily dose level is, of course, lower than the therapeutic level and will preferably be in the range of from 2-20 mg per kilogram of body weight.

The compounds described herein when employed for their anthelmintic activity are useful in the treatment and/or prevention of helminthiasis, a parasitic disease, which causes wide-spread and often serious infection in domesticated animals such as swine, horses, cattle, dogs, cats and sheep. Compounds of the invention are useful in treating infections caused by haemonchus, ostertagia, trichostrongylus, cooperia, nematodirus, bunostomum, strongylorides, oesophagostomum, trichiuris and moniezia. In treating domesticated animals, the compounds are given orally and may be mixed with a nontoxic, edible carrier to form a feed supplement, or be administered in unit dosage forms such as powders, capsule, tablet, boluses, drenches, etc.

In general, the compounds of this invention (I) exhibit anthelmintic acitvity when administered to animals in a daily dose of about 10 to about 200 mg per kilogram of animal body weight. It is preferred to employ in the range of 20-100 mg per kilogram of body weight per day. The compounds may be given in a single dose or divided into a plurality of smaller doses. When the compounds are to be employed primarily as agents for the prevention of helminthic infections the preferred daily dose level is, of course, lower than the therapeutic level is, preferably in the range of about 2-20 mg per kilogram of body weight.

When the compounds of this invention are to be administered in unit dosage form, capsules, boluses or drenches containing the desired amount of anthelmintic, anti-bacterial or antifungal agent distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

DETAILED DESCRIPTION

The following examples are provided for illustrative purposes and may include particular features of the invention; however, the examples should not be construed as limiting the invention, many variations of which are possible without departing from the spirit or scope thereof. The temperatures set out in such examples are all in degrees Centigrade.

EXAMPLE 1

2-Thiopheneamidoxime

To a solution of 21.8 g (0.20 mole) of 2-cyanothiophene in 500 ml of ethanol, 13.9 g (0.20 mole) of hydroxylamine HCl is added, followed by the addition of 13.8 g (0.10 mole) of $K_2CO_3$ in 50 ml of water. The mixture is refluxed for 16 hours, cooled and diluted with 200 ml of water. After removing the ethanol in vacuo, the product precipitates out of the aqueous residue. It is collected by filtration, washed with water and dried to yield 22.4 g (80%) of product, m.p. 70°–75°.

EXAMPLE 2

5-(4-Nitrophenyl)-3-(2-thienyl)-1,2,4-oxadiazole

To a solution of 2-thiopheneamidoxime (10 g, 0.07 mole) and p-nitrobenzoyl chloride (13 g, 0.07 mole) in 400 ml of dry dioxane, 1 ml of $BF_3$-ethyl ether is added and the mixture is heated to reflux for 16 hours. Evaporation of the solvent in vacuo gives a dark solid. It is decolorized by treating with Darco ($CHCl_3$). The solvent is concentrated in vacuo and the product is crystallized from ethanol to give 12.5 g (65%) of product, m.p. 169°–171°.

EXAMPLE 3

5-(4-Aminophenyl)-3-(2-thienyl)-1,2,4-oxadiazole

A suspension of 5-(4-nitrophenyl)-3-(2-thienyl)-1,2,4-oxadiazole (3.1 g, 0.01 mole) in 150 ml of absolute alcohol containing 1.84 ml of concentrated HCl is hydrogenated using 0.4 g of 5% Pd on carbon as catalyst. The solid is slurried with saturated $K_2CO_3$ solution and extracted with chloroform. Evaporation of the chloroform in vacuo gives the amine as a yellow solid, 1.4 g (50% yield).

EXAMPLE 4

5-(4-Isothiocyanophenyl)-3-(2-thienyl)-1,2,4-oxadiazole

To a solution of 1.2 g (0.005 mole) of 5-(4-aminophenyl)-3-(2-thienyl)-1,2,4-oxadiazole in 150 ml of dry tetrahydrofuran containing 0.49 g of triethylamine, 0.56 g (0.005 mole) of thiophosgene is added and the mixture stirred at room temperature for 3 hours. After filtration, the solution is evaporated in vacuo to give the crude product. It is crystallized from petroleum ether to give 0.7 g (50%) of the title compound, m.p. 161°–162°.

EXAMPLE 5

3-(2-Furyl)-5-(4-nitrophenyl)-1,2,4-oxadiazole

To a solution of 2-furanamidoxime (12.6 g, 0.1 mole) and p-nitrobenzoyl chloride (18.1 g, 0.1 mole) in 500 ml of dry dioxane, 1 ml of $BF_3$-ethyl ether is added and the mixture is heated to reflux for 16 hours. Evaporation of the solvent in vacuo gives a light brown solid. It is decolorized with Darco ($CHCl_3$) and crystallized from ethanol-acetonitrile to give 19.2 g (75%) of product, m.p. 168°–170°.

EXAMPLE 6

3-(2-Furyl)-5-(4-aminophenyl)-1,2,4-oxadiazole

A suspension of 3-(2-furyl)-5-(4-nitrophenyl)-1,2,4-oxadiazole (8.0 g, 0.03 mole) in 200 ml of absolute alcohol containing 5.2 ml of concentrated HCl is hydrogenated using 0.5 g of 5% Pd on carbon as catalyst. The solid obtained is slurried with saturated $K_2CO_3$ solution and extracted with $CHCl_3$. Evaporation of the $CHCl_3$ in vacuo gives the amine, 5.1 g (72%), m.p. 183°–185°.

EXAMPLE 7

3-(2-Furyl)-5-(4-isothiocyanophenyl)-1,2,4-oxadiazole

To a solution of 3-(2-furyl)-5-(4-aminophenyl)-1,2,4-oxadiazole (5.1 g, 0.02 mole) in 150 ml of dry tetrahydrofuran containing 3.1 ml of triethylamine, thiophosgene 2.53 g (0.02 mole) is added and the mixture is stirred at room temperature for 4 hours. After filtration, the solvent is evaporated in vacuo and the product is crystallized from petroleum ether to give 4.0 g (68%) of the title compound, m.p. 136°–137°.

EXAMPLE 8

4-Chloro-3-nitrobenzoyl chloride

To a solution of 14.1 g (0.07 mole) of 4-chloro-3-nitrobenzoic acid in 200 ml of dry benzene, 10 ml of thionyl chloride is added and the mixture is refluxed for 10 hours. The excess of thionyl chloride is removed in vacuo and the acid chloride is purified by repeated addition of fresh benzene and subsequent removal in vacuo.

EXAMPLE 9

5-(4-Chloro-3-nitrophenyl)-3-(2-furyl)-1,2,4-oxadiazole

Following the procedure of Example 5, but substituting 4-chloro-3-nitrobenzoyl chloride for p-nitrobenzoyl chloride, the title product is obtained, m.p. 136°–137°.

EXAMPLE 10

5-(4-Chloro-3-aminophenyl)-3-(2-furyl)-1,2,4-oxadiazole

Following the procedure of Example 6, but substituting 5-(4-chloro-3-nitrophenyl)-3-(2-furyl)-1,2,4-oxadiazole for 3-(2-furyl)-5-(4-nitrophenyl)-1,2,4-oxadiazole, the title product is obtained, m.p. 203°–204°. (55% Yield).

EXAMPLE 11

5-(4-Chloro-3-isothiocyanophenyl)-3-(2-furyl)-1,2,4-oxadiazole

To a solution of 4.8 g of 5-(4-chloro-3-aminophenyl)-3-(2-furyl)-1,2,4-oxadiazole in 400 ml of tetrahydrofuran, 5 ml of triethylamine and 2.1 g of thiophosgene are added. After stirring at room temperature for 4 hours, the reaction mixture is filtered and evaporated to dryness in vacuo. The residue is crystallized from petroleum ether to yield 1.5 g (27%) of the title product, m.p. 131°–132°.

EXAMPLE 12

5-(4-Nitrophenyl)-3-(2-pyridyl)-1,2,4-oxadiazole

A mixture of 10 g (0.07 mole) of 2-pyridylamidoxime and 13.3 g (0.07 mole) of p-nitrobenzoyl chloride in 1.1 liters of dry dioxane containing 1 ml of BF$_3$-ethyl ether is refluxed for 24 hours. Evaporation of the solvent in vacuo gives a dark solid. It is dissolved in chloroform and decolorized with Darco. The solvent is evaporated in vacuo and the solid is crystallized from ethanol to give 8.6 g of product (45% yield), m.p. 211°–213°.

EXAMPLE 13

5-(4-Aminophenyl)-3-(2-pyridyl)-1,2,4-oxadizole

A solution of 2.5 g (0.01 mole) of 5-(4-nitrophenyl)-3-(2-pyridyl)-1,2,4-oxadiazole in 200 ml of tetrahydrofuran is added slowly to a solution of NaBH$_2$S$_3$ which is prepared by stirring 0.36 g of NaBH$_4$ and 0.96 g of sulfur in 50 ml of tetrahydrofuran for 0.5 hour. The reaction mixture is then refluxed for 24 hours. The mixture is filtered, cooled, and the solvent is evaporated in vacuo to give 1.0 g (42% yield) of the title compound.

EXAMPLE 14

5-(4-Isothiocyanophenyl)-3-(2-pyridyl)-1,2,4-oxadiazole

To a solution of 1.09 g of 5-(4-aminophenyl)-3-(2-pyridyl)-1,2,4-oxadiazole in 200 ml of dry tetrahydrofuran containing 0.42 g of triethylamine, 0.50 g of thiophosgene is added and the mixture stirred at room temperature for 6 hours. After filtration, the solution is evaporated in vacuo to give the crude product. It is crystallized from petroleum ether to give 0.65 g (54%) of the title product, m.p. 145°–146°.

EXAMPLE 15

5-(4-Nitrophenyl)-3-(3-pyridyl)-1,2,4-oxadiazole

Following the procedure of Example 12, but substituting 3-pyridylamidoxime for 2-pyridylamidoxime, the title product is obtained in 56% yield, m.p. 163°–166°.

EXAMPLE 16

5-(4-Aminophenyl)-3-(3-pyridyl)-1,2,4-oxadiazole

A solution of 5-(4-nitrophenyl)-3-(3-pyridyl)-1,2,4-oxadiazole in tetrahydrofuran is reduced according to the procedure of Example 13 to give the title compound in 45% yield.

EXAMPLE 17

5-(4-Isothiocyanophenyl)-3-(3-pyridyl)-1,2,4-oxadiazole

A solution of 5-(4-aminophenyl)-3-(3-pyridyl)-1,2,4-oxadiazole in tetrahydrofuran is reacted with thiophosgene according to Example 14 to give the title compound in 30% yield, m.p. 121°–123°.

EXAMPLES 18 – 33

Substituted-amidoximes

According to the procedures described in Example 1, upon substituting in place of 2-cyanothiophene, one of the nitriles set out in column A below, the corresponding amidoxime shown in column B below is obtained.

TABLE A

| Ex. No. | Column A | Column B |
|---|---|---|
| 18. | 4-cyano-1,3-thiazole | 4-(1,3-thiazole)amidoxime |
| 19. | 2-cyano-N-methylpyrrole | 2-(N-methylpyrrole)amidoxime |
| 20. | 2-cyano-1,3-thiazole | 2-(1,3-thiazole)amidoxime |
| 21. | 2-cyanopyrazine | 2-pyrazineamidoxime |
| 22. | 2-cyanopyrimidine | 2-pyrimidineamidoxime |
| 23. | 4-cyanoquinoline | 4-quinolineamidoxime |
| 24. | 5-cyano-1,3-imidazole | 5-(1,3-imidazole)amidoxime |
| 25. | 5-cyano-1,3-oxazole | 5-(1,3-oxazole)amidoxime |
| 26. | 4-cyano-1,2-thiazole | 4-(1,2-thiazole)amidoxime |
| 27. | 3-cyanopyrrole | 3-pyrroleamidoxime |
| 28. | 2-cyanopyridine | 3-pyridineamidoxime |
| 29. | 2-cyano-3-chlorofuran | 2-(3-chlorofuran)amidoxime |
| 30. | 2-cyano-1,4-N,N-dimethyl-piperazine | 2-(1,4-N,N-dimethylpiperazine)-amidoxime |
| 31. | 3-cyano-1,4-N,N-diethyl-piperazine | 3-(1,4-N,N-diethylpiperazine)-amidoxime |
| 32. | 2-cyano-1,3,4-thiadiazole | 2-(1,3,4-thiadiazole)amidoxime |
| 33. | 5-cyano-1,2,4-triazole | 5-(1,2,4-triazole)amidoxime |

EXAMPLES 34 – 55

Following the procedure described in Example 2, but substituting the amidoxime shown in column A of Table B set out below and the nitrobenzoyl chloride shown in column B, the 5-nitrophenyl-1,2,4-oxadiazole shown in column C is obtained.

TABLE B

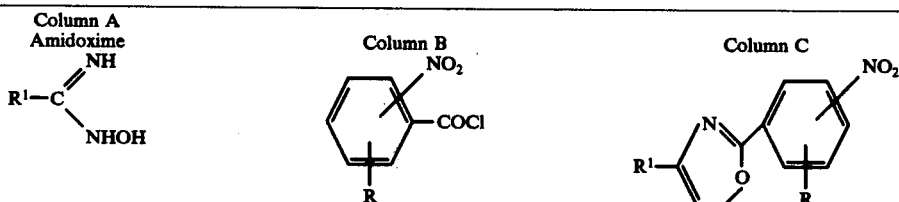

| Ex. No. | R$^1$ | R | NO$_2$ (position) | R$^1$ | R | NO$_2$ (position) |
|---|---|---|---|---|---|---|
| 34. | [N,S-thiazole] | (prepared as per Ex. 18) H | p- | [N,S-thiazole] | H | p- |
| 35. | " | H | m- | " | H | m- |
| 36. | " | H | o- | " | H | o- |
| 37. | " | o-Cl | p- | " | 2-Cl | 4- |
| 38. | [N,S-thiazole] | (prepared as per Ex. 18) m-Cl | p- | [N,S-thiazole] | 3-Cl | 4- |
| 39. | " | " | m-CH$_3$ | p- | " | 3-CH$_3$ | 4- |

TABLE B-continued

| | Column A Amidoxime $R^1-C(=NH)NHOH$ | | Column B 2-nitro-benzoyl chloride with R | | Column C oxadiazole product | | |
|---|---|---|---|---|---|---|---|
| Ex. No. | $R^1$ | | R | $NO_2$ (position) | $R^1$ | R | $NO_2$ (position) |
| 40. | " | | o-$C_2H_5O$ | p- | " | 2-$C_2H_5O$ | 4- |
| 41. | 1-methyl-pyrrolinyl (CH₃-N) | (prepared as per Ex. 19) | H | m- | 1-methyl-pyrrolinyl | H | 3- |
| 42. | 2-methyl-thiazolyl | (prepared as per Ex. 20) | m-Cl | p- | 2-methyl-thiazolyl | 3-Cl | 4- |
| 43. | methylpyrazinyl | (prepared as per Ex. 21) | H | p- | methylpyrazinyl | H | 4- |
| 44. | 2-methylpyrimidinyl | (prepared as for Ex. 22) | H | p- | 2-methylpyrimidinyl | H | 4- |
| 45. | quinolinyl | (prepared as for Ex. 23) | H | p- | quinolinyl | H | 4- |
| 46. | imidazolyl-CH(CH₃)- | (prepared as per Ex. 24) | m-$C_6H_5$ | p- | imidazolyl-CH(CH₃)- | 3-$C_6H_5$ | 4- |
| 47. | methyl-oxazolyl | (prepared as per Ex. 25) | o-$CF_3$ | m- | methyl-oxazolyl | 2-$CF_3$ | 3- |
| 48. | methyl-isothiazolyl | (prepared as per Ex. 26) | p-$C_6H_5O$ | o- | methyl-isothiazolyl | 4-$C_6H_5O$ | 2- |
| 49. | pyrrolyl | (prepared as per Ex. 27) | p-$N(CH_3)_2$ | o- | pyrrolyl | 4-$N(CH_3)_2$ | 2- |
| 50. | 3-chloro-2-methylfuryl | (prepared as per Ex. 29) | H | p- | 3-chloro-2-methylfuryl | H | 4- |
| 51. | pyridyl | (prepared as per Ex. 28) | o—CH₃CN(H)C(=O)— | p- | pyridyl | 2—CH₃CN(H)C(=O)— | 4- |
| 52. | 1,4-dimethylpiperazinyl | (prepared as per Ex. 30) | o-$C_2H_5$ | p- | 1,4-dimethylpiperazinyl | 2-$C_2H_5$ | 4- |
| 53. | $C_2H_5$-N / NH—$C_2H_5$ methyl piperazinyl | (prepared as per Ex. 31) | m-Br | p- | same | 3-Br | 4- |
| 54. | thiadiazolyl | (prepared as per Ex. 33) | H | p- | thiadiazolyl | H | p- |

TABLE B-continued

| | Column A Amidoxime R¹—C(=NH)NHOH | | Column B (NO₂, COCl on phenyl with R) | | Column C (oxadiazole with R¹, NO₂, R) | |
|---|---|---|---|---|---|---|
| Ex. No. | R¹ | R | NO₂ (position) | R¹ | R | NO₂ (position) |
| 55. | H-N-N=N (triazolyl-H) | (prepared as per Ex. 34) | o-Cl | p- | H-N-N=N (triazolyl-H) | 2-Cl | 4- |

EXAMPLES 56 – 77

Following the procedure of Example 3 but substituting for the 5-(4-nitrophenyl)-3-(2-thienyl)-1,2,4-oxadiazole, each of the 3-hetero-5-nitrophenyl-1,2,4-oxadiazoles of Examples 34–55, the corresponding 3-hetero-5-aminophenyl-1,2,4-oxadiazoles are obtained as set out below:

| Ex. No. | 3-Hetero-5-aminophenyl-1,2,4-oxadiazole |
|---|---|
| 56. | 5-(4-aminophenyl)-3-(4-thiazolyl)-1,2,4-oxadiazole |
| 57. | 5-(3-aminophenyl)-3-(4-thiazolyl)-1,2,4-oxadiazole |
| 58. | 5-(2-aminophenyl)-3-(4-thiazolyl)-1,2,4-oxadiazole |
| 59. | 5-(4-amino-2-chlorophenyl)-3-(4-thiazolyl)-1,2,4-oxadiazole |
| 60. | 5-(4-amino-3-chlorophenyl)-3-(4-thiazolyl)-1,2,4-oxadiazole |
| 61. | 5-(4-amino-3-methylphenyl)-3-(4-thiazolyl)-1,2,4-oxadiazole |
| 62. | 5-(4-amino-2-ethoxyphenyl)-3-(4-thiazolyl)-1,2,4-oxadiazole |
| 63. | 5-(3-aminophenyl)-3-(2-N-methylpyrryl)-1,2,4-oxadiazole |
| 64. | 5-(4-amino-3-chlorophenyl)-3-(2-thiazolyl)-1,2,4-oxadiazole |
| 65. | (5-(4-aminophenyl)-3-(2-pyrazinyl)-1,2,4-oxadiazole |
| 66. | 5-(4-aminophenyl)-3-(2-pyrimidinyl)-1,2,4-oxadiazole |
| 67. | 5-(4-aminophenyl)-3-(4-quinolinyl)-1,2,4-oxadiazole |
| 68. | 5-[4-amino-(3-phenyl)phenyl]-3-[4(5)-imidazolyl]-1,2,4-oxadiazole |
| 69. | 5-(3-amino-2-trifluoromethylphenyl)-3-(2-oxazolyl)-1,2,4-oxadiazole |
| 70. | 5-(2-amino-4-phenoxyphenyl)-3-(2-isothiazolyl)-1,2,4-oxadiazole |
| 71. | 5-(2-amino-4-dimethylaminophenyl)-3-(3-pyrryl)-1,2,4-oxadiazole |
| 72. | 5-(4-aminophenyl)-3-[2-(5-chloro-2-furyl)]-1,2,4-oxadiazole |
| 73. | 5-(4-amino-2-methylcarboxamidophenyl)-3-(3-pyridyl)-1,2,4-oxadiazole |
| 74. | 5-(4-amino-2-ethylphenyl)-3-(2,5-N,N-dimethylpiperazinyl)-1,2,4-oxadiazole |
| 75. | 5-(4-amino-3-bromophenyl)-3-[2,5-(N,N-diethylpiperazinyl)]-1,2,4-oxadiazole |
| 76. | 5-(4-aminophenyl)-3-(2-thiadiazolyl)-1,2,4-oxadiazole |
| 77. | 5-(4-amino-2-chlorophenyl)-3-(2-triazolyl)-1,2,4-oxadiazole |

EXAMPLES 78 – 99

Following the procedure of Example 4 but substituting for the 5-(4-aminophenyl)-3-(2-thienyl)-1,2,4-oxadiazole, each of the 3-hetero-5-aminophenyl-1,2,4-oxadiazoles of Examples 56–77, the corresponding 3-hetero-5-isothiocyanophenyl-1,2,4-oxadiazoles are obtained as set out below:

| Ex. No. | 3-Hetero-5-aminophenyl-1,2,4-oxadiazole |
|---|---|
| 78. | 5-(4-isothiocyanophenyl)-3-(4-thiazolyl)-1,2,4-oxadiazole |
| 79. | 5-(3-isothiocyanophenyl)-3-(4-thiazolyl)-1,2,4-oxadiazole |
| 80. | 5-(2-isothiocyanophenyl)-3-(4-thiazolyl)-1,2,4-oxadiazole |
| 81. | 5-(4-isothiocyano-2-chlorophenyl)-3-(4-thiazolyl)-1,2,4-oxadiazole |
| 82. | 5-(4-isothiocyano-3-chlorophenyl)-3-(4-thiazolyl)-1,2,4-oxadiazole |
| 83. | 5-(4-isothiocyano-3-methylphenyl)-3-(4-thiazolyl)-1,2,4-oxadiazole |
| 84. | 5-(4-isothiocyano-2-ethoxyphenyl)-3-(4-thiazolyl)-1,2,4-oxadiazole |
| 85. | 5-(3-isothiocyanophenyl)-3-(2-N-methylpyrryl)-1,2,4-oxadiazole |
| 86. | 5-(4-isothiocyano-3-chlorophenyl)-3-(2-thiazolyl)-1,2,4-oxadiazole |
| 87. | 5-(4-isothiocyanophenyl)-3-(2-pyrazinyl)-1,2,4-oxadiazole |
| 88. | 5-(4-isothiocyanophenyl)-3-(2-pyrimidinyl)-1,2,4-oxadiazole |
| 89. | 5-(4-isothiocyanophenyl)-3-(4-quinolinyl)-1,2,4-oxadiazole |
| 90. | 5-(4-isothiocyano-3-diphenyl)-3-(4-imidazolyl)-1,2,4-oxadiazole |
| 91. | 5-(3-isothiocyano-2-trifluoromethylphenyl)-3-(2-oxazolyl)-1,2,4-oxadiazole |
| 92. | 5-(2-isothiocyano-4-phenoxyphenyl)-3-(2-isothiazolyl)-1,2,4-oxadiazole |
| 93. | 5-(2-isothiocyano-4-dimethylaminophenyl)-3-(3-pyrryl)-1,2,4-oxadiazole |
| 94. | 5-(4-isothiocyanophenyl)-3-[2-(5-chloro-2-furyl)]-1,2,4-oxadiazole |
| 95. | 5-(4-isothiocyano-2-methylcarboxamidophenyl)-3-(3-pyridyl)-1,2,4-oxadiazole |
| 96. | 5-(4-isothiocyano-2-ethylphenyl)-3-(2,5-N,N-dimethyl)piperazinyl)-1,2,4-oxadiazole |
| 97. | 5-(4-isothiocyano-3-bromophenyl)-3-[2,5-(N,N-diethylpiperazinyl)]-1,2,4-oxadiazole |
| 98. | 5-(4-isothiocyanophenyl)-3-(2-thiadiazolyl)-1,2,4-oxadiazole |
| 99. | 5-(4-isothiocyano-2-chlorophenyl)-3-(2-triazolyl)-1,2,4-oxadiazole |

What is claimed is:

1. A method for treating fungal infections and/or bacterial infections, which comprises administering to a mammalian host an effective amount of a compound of the formula

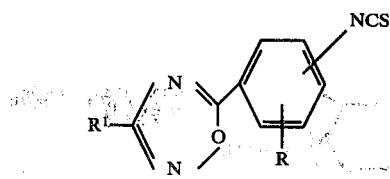

wherein R is selected from the group consisting of hydrogen, lower alkyl, halogen, trifluoromethyl, lower alkoxy, phenoxy, di(lower alkyl)amino, lower alkyl 

phenyl, or phenyl substituted with halogen, nitro, trifluoromethyl, lower alkyl or lower alkoxy, $R^1$ is a heterocyclic group selected from the group consisting of thienyl, furyl, pyrryl, imidazolyl, oxazolyl, and any of the above groups substituted by lower alkyl substituent, a lower alkoxy substituent or a halo substituent.

2. The method as defined in claim 1 wherein R is selected from the group consisting of hydrogen, halogen, lower alkyl, and lower alkoxy.

3. The method as defined in claim 1 wherein $R^1$ is selected from the group consisting of thienyl and furyl.

4. The method as defined in claim 1 wherein $R^1$ is N-alkyl-pyrryl.

5. The method as defined in claim 1 wherein the SCN-group is in the 4-position.

6. The method as defined in claim 1 wherein R is selected from the group consisting of hydrogen, 2- or 3-chloro, 2- or 3-lower alkyl, and 2- or 3-lower alkoxy.

7. The method in accordance with claim 1 wherein the compound employed has the name 5-(4-isothiocyanophenyl)-3-(2-thienyl)-1,2,4-oxadiazole.

8. The method in accordance with claim 1 wherein the compound employed has the name 3-(2-furyl)-5-(4-isothiocyanophenyl)-1,2,4-oxadiazole.

9. The method in accordance with claim 1 wherein the compound employed has the name 5-(4-chloro-3-isothiocyanohenyl)-3-(2-furyl)-1,2,4-oxadiazole.

* * * * *

UNITED STATES PATENT OFFICE
CERTIFICATE OF CORRECTION

Patent No. 4,065,563      Dated December 27, 1977

Inventor(s) Venkatachala L. Narayanan et al

It is certified that error appears in the above-identified patent and that said Letters Patent are hereby corrected as shown below:

Columns 9 and 10, Example 45, the two structures should read

-- 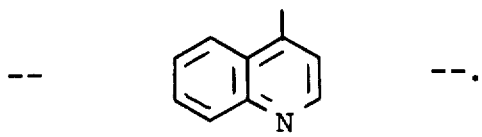 --.

Column 11, Example 65, delete the "(" at the beginning of the example.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks